(12) United States Patent
Mizutani et al.

(10) Patent No.: US 7,354,425 B2
(45) Date of Patent: Apr. 8, 2008

(54) INTERLABIAL PAD

(75) Inventors: Satoshi Mizutani, Kagawa (JP); Koichi Yamaki, Kagawa (JP); Yuki Noda, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 31 days.

(21) Appl. No.: 10/705,780

(22) Filed: Nov. 10, 2003

(65) Prior Publication Data
US 2004/0147895 A1 Jul. 29, 2004

Related U.S. Application Data

(63) Continuation of application No. PCT/JP02/04883, filed on May 21, 2002.

(30) Foreign Application Priority Data
May 22, 2001 (JP) ............................. 2001-152403
Aug. 8, 2001 (JP) ............................. 2001-241251

(51) Int. Cl.
*A61F 13/15* (2006.01)
(52) U.S. Cl. ........................ 604/385.17; 604/385.18; 604/904; 604/385.101; 604/378
(58) Field of Classification Search ........... 604/385.17, 604/385.18, 904, 378, 379, 385.101, 385.01
See application file for complete search history.

(56) References Cited
U.S. PATENT DOCUMENTS

| | | | |
|---|---|---|---|
| 2,331,355 A | 9/1943 | Strongson | |
| 4,595,392 A | 6/1986 | Johnson et al. | |
| 5,057,096 A | 10/1991 | Faglione | |
| 5,868,727 A | 2/1999 | Barr et al. | |
| 5,916,205 A | 6/1999 | Olson et al. | |
| 6,131,575 A | 10/2000 | Lenker et al. | |
| 6,131,736 A | 10/2000 | Farris et al. | |
| 6,461,340 B1 * | 10/2002 | Lenker et al. | 604/385.17 |

FOREIGN PATENT DOCUMENTS

| | | |
|---|---|---|
| EP | 0888764 | 1/1999 |
| EP | 1 051 956 A1 | 11/2000 |
| EP | 1 097 685 A2 | 5/2001 |
| JP | 493722 | 1/1974 |
| JP | 61-149145 | 7/1986 |
| JP | 108258 | 7/1986 |

(Continued)

OTHER PUBLICATIONS

Mizutani, et al., "Interlabial Pad", U.S. Appl. No. 10/705,403, filed Nov. 10, 2003.

(Continued)

Primary Examiner—Jacqueline F. Stephens
(74) Attorney, Agent, or Firm—Darby & Darby P.C.

(57) ABSTRACT

The present invention relates to an interlabial pad which is used by being fitted between labia of a user for absorbing the menstrual blood, and provides an interlabial pad which can surely absorb even a high-speed, large-volume menstrual blood, flowing down the body along inner labial walls. An interlabial pad (14) is devised to provide an protruded area (14*b*) in a part of a flat area (14*a*), having an absorbing function, and the ratio of the protruded area (14*b*) and the flat area (14*a*) is controlled accurately.

15 Claims, 12 Drawing Sheets

FOREIGN PATENT DOCUMENTS

| | | |
|---|---|---|
| JP | 63260556 | 10/1988 |
| JP | 0356366 | 3/1991 |
| JP | 05237151 | 9/1993 |
| JP | 05293138 | 11/1993 |
| JP | 6-506368 A1 | 7/1994 |
| JP | 0640203 | 10/1994 |
| JP | 08-215242 A1 | 8/1996 |
| JP | 9-99009 A1 | 4/1997 |
| JP | 2000-051267 | 12/1999 |
| JP | 2001-509402 | 7/2001 |
| JP | 2002-513633 A1 | 7/2001 |
| JP | 02534163 | 10/2002 |
| TW | 179256 A1 | 2/1992 |
| TW | 247431 A1 | 5/1995 |
| TW | 294591 A1 | 1/1997 |
| TW | 338315 A1 | 8/1998 |
| TW | 416847 A1 | 1/2000 |
| TW | 386030 A1 | 4/2000 |
| TW | 386872 A1 | 4/2000 |
| TW | 394681 A1 | 6/2000 |
| TW | 442278 A1 | 6/2001 |
| TW | 450802 A1 | 8/2001 |
| TW | 454503 A1 | 9/2001 |
| TW | 470640 A1 | 1/2002 |
| TW | 524677 A1 | 3/2003 |
| WO | WO 92/11825 | 7/1992 |
| WO | 9500094 A1 | 1/1995 |
| WO | 95/17148 A2 | 6/1995 |
| WO | WO-98/25524 B1 | 6/1998 |
| WO | WO-99/01096 A1 | 1/1999 |
| WO | WO-99/15123 A1 | 4/1999 |
| WO | WO-99/26574 | 6/1999 |
| WO | WO-99/55270 A1 | 11/1999 |
| WO | WO 99/56681 | 11/1999 |
| WO | WO 0040192 | 7/2000 |
| WO | 0147458 A1 | 7/2001 |

OTHER PUBLICATIONS

Mizutani, et al., "Interlabial Pad", U.S. Appl. No. 10/705,811, filed Nov. 10, 2003.

Mizutani, et al., "Flap-Equipped Interlabial Pad", U.S. Appl. No. 10/705,670, filed Nov. 10, 2003.

Mizutani, Satoshi, "Interlabial Product Having Form for Finger Securement, and Individual Package", U.S. Appl. No. 10/705,779, filed Nov. 10, 2003.

Mizutani, et al., "Interlabial Pad Individual Packaging Body", U.S. Appl. No. 10/705,669, filed Nov. 10, 2003.

Mizutani, et al., "Individual Packaging Body and Outer Vessel Therefor", U.S. Appl. No. 10/705,402, filed Nov. 10, 2003.

Mizutani, et al., "Interlabial Pad and Package Thereof", U.S. Appl. No. 10/705,404, filed Nov. 10, 2003.

Mizutani, et al., "Interlabial Pad", U.S. Appl. No. 10/705,406, filed Nov. 10, 2003.

Mizutani, et al., "Interlabial Pad and Package Thereof", U.S. Appl. No. 10/705,810, filed Nov. 10, 2003.

Mizutani, et al., "Interlabial Pad", U.S. Appl. No. 10/705,408, filed Nov. 10, 2003.

Mizutani, et al., "Interlabial Pad", U.S. Appl. No. 10/705,407, filed Nov. 10, 2003.

Mizutani, et al., "Interlabial Pad", U.S. Appl. No. 10/705,812, filed Nov. 10, 2003.

Mizutani, et al., "Interlabial Pad", U.S. Appl. No. 10/705,778, filed Nov. 10, 2003.

Mizutani, et al., "Interlabial Pad Individual Packaging Vessel, and Individual Packaging Body", U.S. Appl. No. 10/705,781, filed Nov. 10, 2003.

Mizutani, et al., "Interlabial Pad and Package Thereof", U.S. Appl. No. 10/705,400, filed Nov. 10, 2003.

Mizutani, et al., "Interlabial Pad", U.S. Appl. No. 10/705,399, filed Nov. 10, 2003.

Mizutani, et al, "Interlabial Pad and Package", U.S. Appl. No. 10/706,303, filed Nov. 10, 2003.

Mizutani, et al., "Interlabial Pad and Package", U.S. Appl. No. 10/706,303, filed Nov. 10, 2003.

Mizutani, et al., "Interlabial Pad", U.S. Appl. No. 10/705,403, Nov. 10, 2003.

Mizutani, et al., "Interlabial Pad", U.S. Appl. No. 10/705,811, Nov. 10, 2003.

Mizutani, et al., "Flap-Equipped Interlabial Pad", U.S. Appl. No. 10/705,670, Nov. 10, 2003.

Mizutani, Satoshi, "Interlabial Product Having Form for Finger Securement, and Individual Package", U.S. Appl. No. 10/705,779, Nov. 10, 2003.

Mizutani, et al., "Interlabial Pad Individual Packaging Body", U.S. Appl. No. 10/705,669, Nov. 10, 2003.

Mizutani, et al., "Individual Packaging Body and Outer Vessel Therefor", U.S. Appl. No. 10/705,402, Nov. 10, 2003.

Mizutani, et al., "Interlabial Pad and Package Thereof", U.S. Appl. No. 10/705,404, Nov. 10, 2003.

Mizutani, et al., "Interlabial Pad", U.S. Appl. No. 10/705,406, Nov. 10, 2003.

Mizutani, et al., "Interlabial Pad and Package Thereof", U.S. Appl. No. 10/705,810, Nov. 10, 2003.

Mizutani, et al., "Interlabial Pad", U.S. Appl. No. 10/705,408, Nov. 10, 2003.

Mizutani, et al., "Interlabial Pad", U.S. Appl. No. 10/705,407, Nov. 10, 2003.

Mizutani, et al., "Interlabial Pad", U.S. Appl. No. 10/705,812, Nov. 10, 2003.

Mizutani, et al., "Interlabial Pad", U.S. Appl. No. 10/705,778, Nov. 10, 2003.

Mizutani, et al., "Interlabial Pad and Package Thereof", U.S. Appl. No. 10/705,400, Nov. 10, 2003.

Mizutani, et al., "Interlabial Pad and Package Thereof", U.S. Appl. No. 10/705,400, Nov. 10, 2003.

Mizutani, et al., "Interlabial Pad", U.S. Appl. No. 10/705,399, Nov. 10, 2003.

Mizutani, et al., "Interlabial Pad and Package", U.S. Appl. No. 10/705,303, Nov. 10, 2003.

Mizutani, et al., "Interlabial Pad and Package", U.S. Appl. No. 10/705,303, Nov. 10, 2003.

\* cited by examiner

FIG. 1
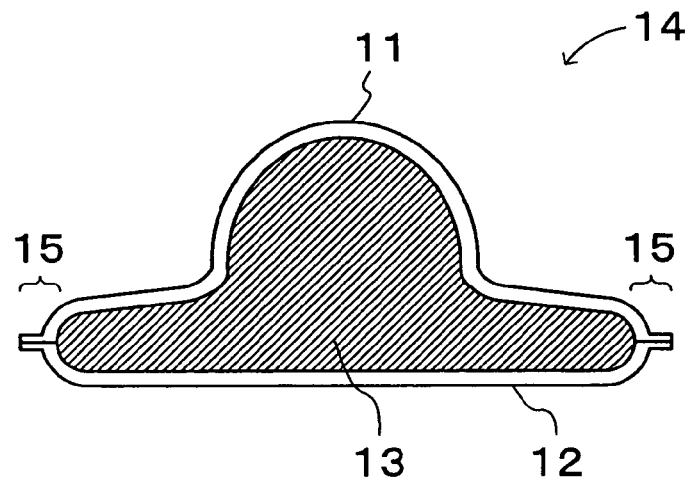
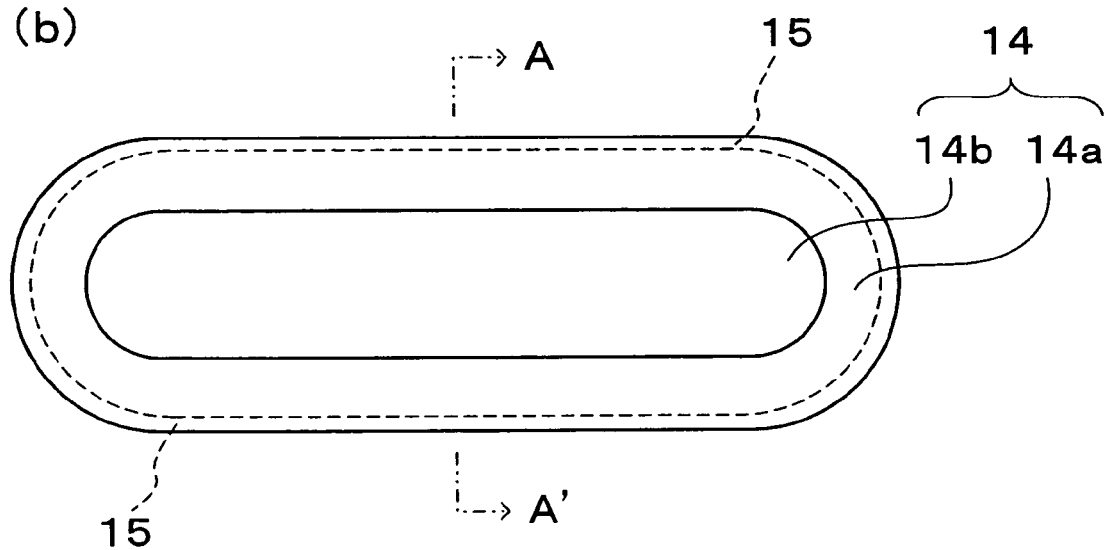

FIG. 3
(a)
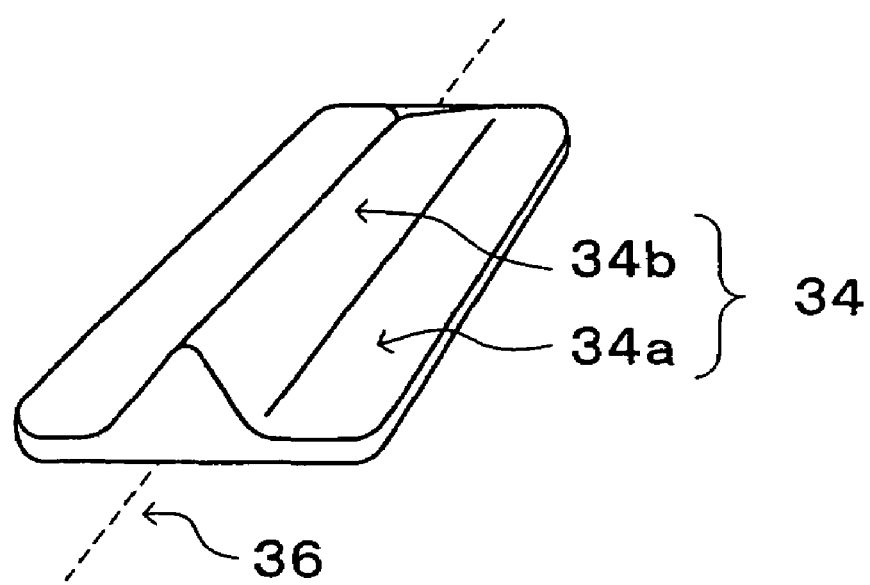
(b)
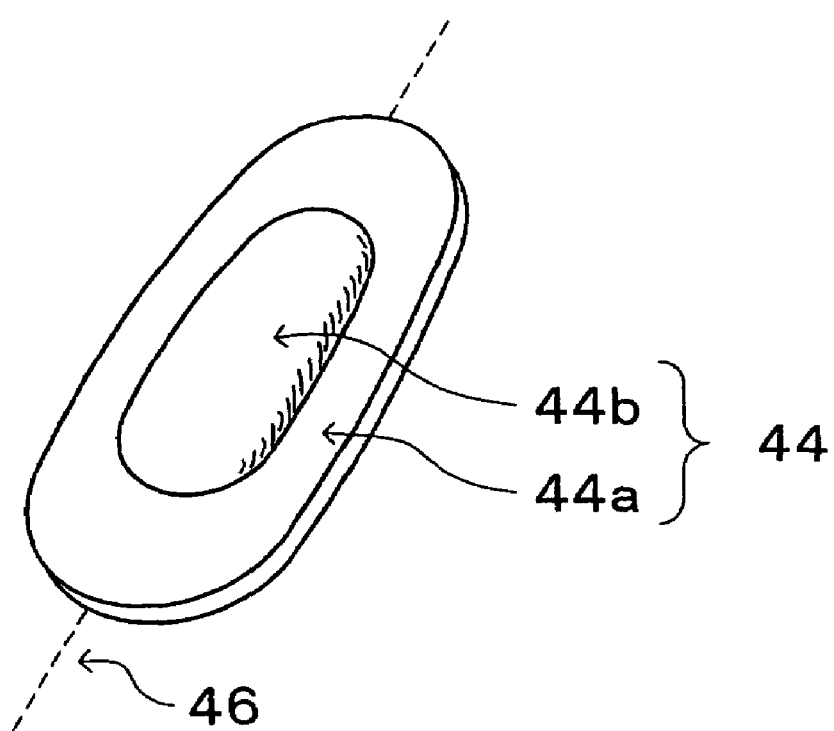

FIG. 4
(a)
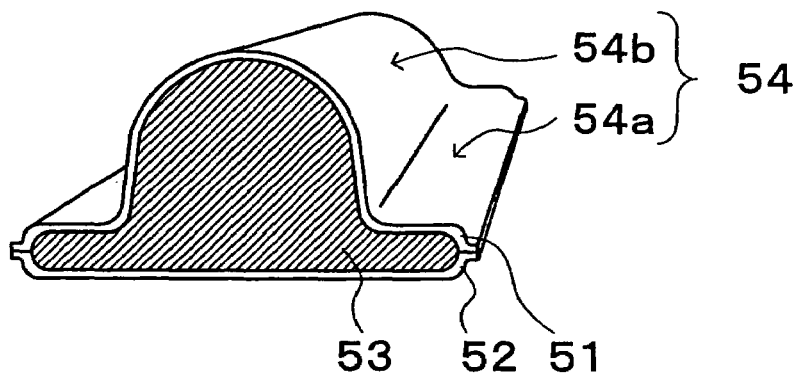
(b)
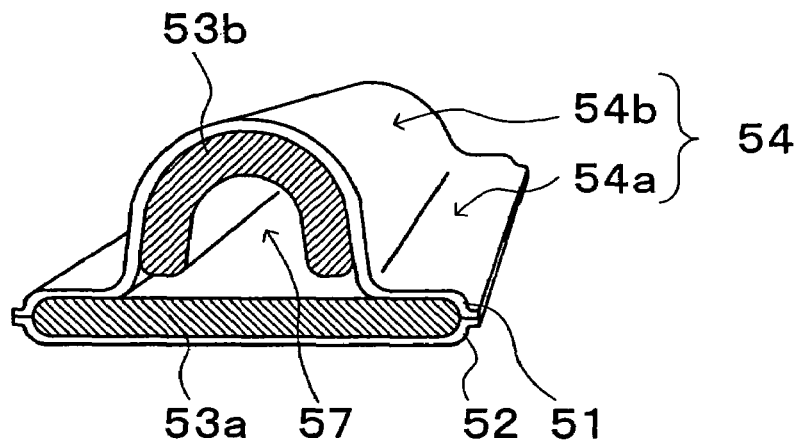
(c)
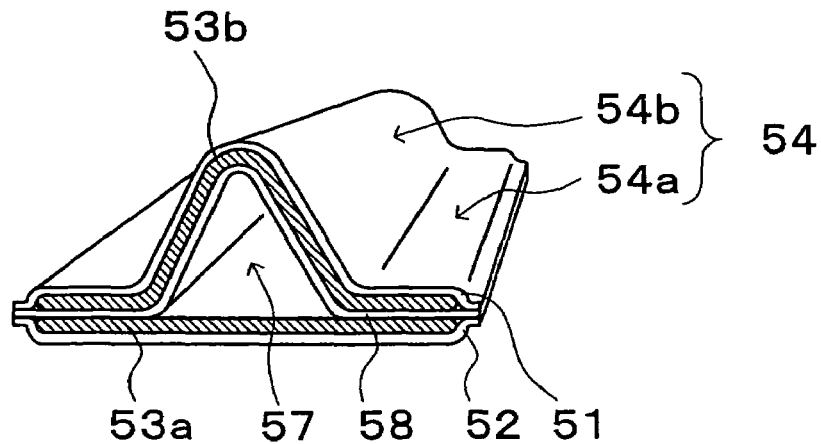

FIG. 8
(a)
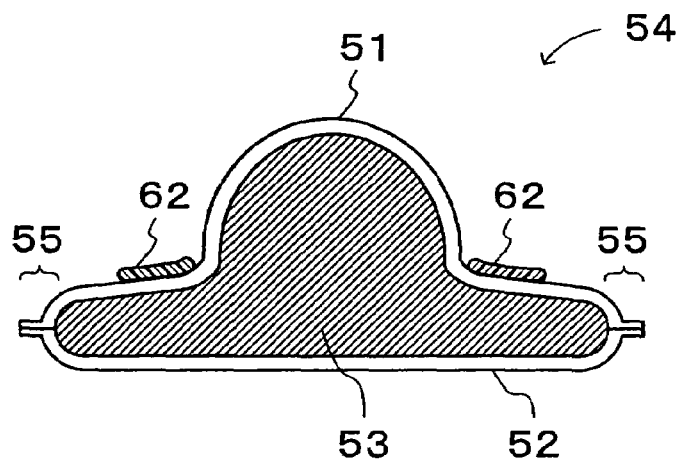
(b)
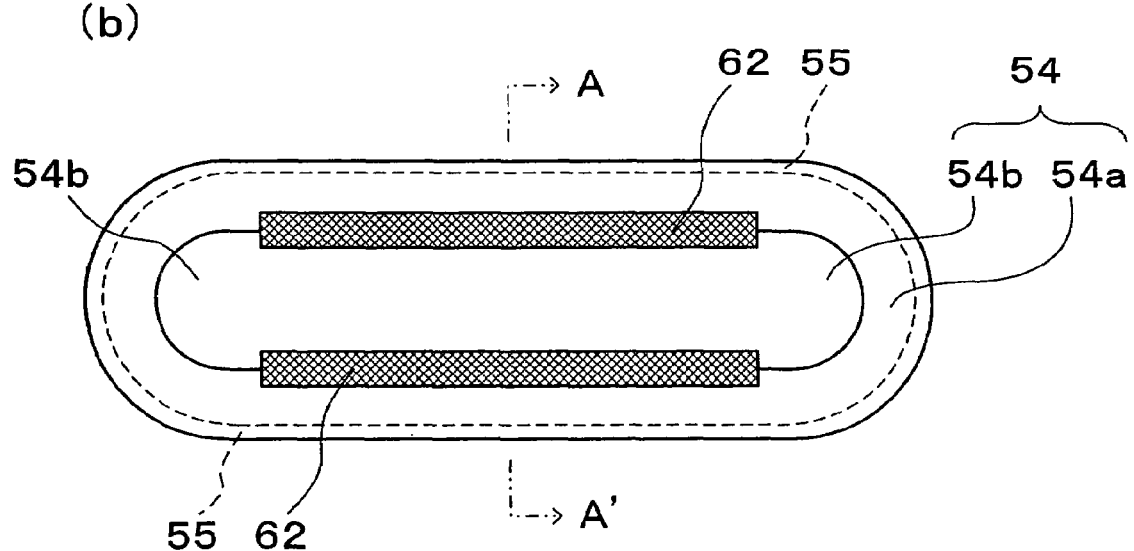

FIG. 9
(a)
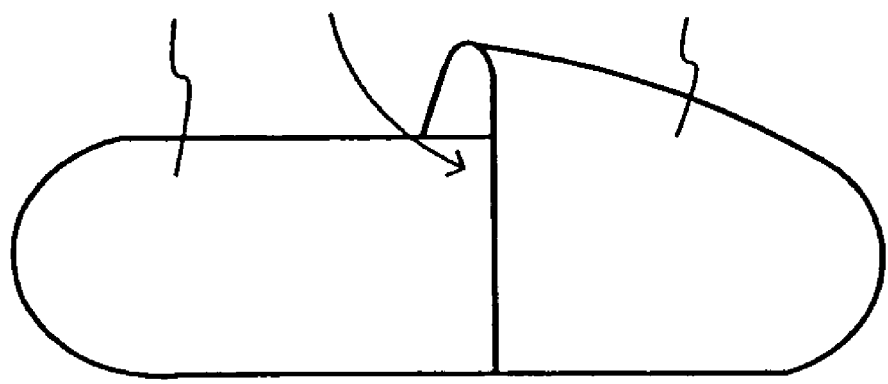
(b)
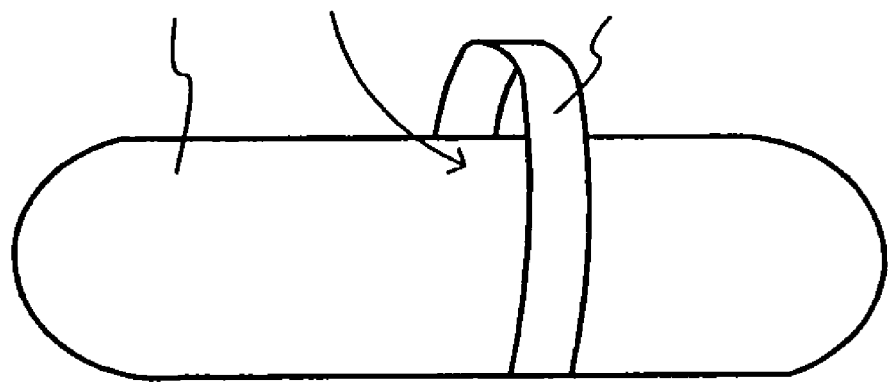

INTERLABIAL PAD

CROSS-REFERENCE TO RELATED APPLICATIONS

This application is a Continuation of International Application No. PCT/JP02/04883 filed May 21, 2002, which application published in Japanese on Nov. 28, 2002 as WO 02/094147 A1 under PCT Article 21(2).

BACKGROUND OF THE INVENTION

1. Technical Field

The present invention relates to an interlabial pad which is attached between the labia to absorb menstrual blood, and more particularly, to the structure of an interlabial pad which reliably absorbs menstrual blood which flows down along the inner walls of the labia, rapidly and in a large quantity.

2. Background Art

Conventionally, a sanitary napkin and a tampon are used generally as female sanitary products. However, there have been problems that as for the sanitary napkin used by bringing into contact with clothes, it tends to cause the leak of menstrual blood from the gap caused by poor adhesion near the ostium vaginae, while it tends to cause the foreign feeling and the discomfort as for the tampon, on the basis of the nature of its products when wearing it, and it is difficult to fix into the vagina.

Under such situation, sanitary products of the interlabial pad have attracted people as a sanitary product positioned between the sanitary napkin and the tampon in recent years.

The interlabial pad is used by inserting its portion between the labia and bringing into contact with the labia, having characteristics that it is difficult to cause the leak of menstrual blood because of higher adhesion to the body than that of the sanitary napkin and psychological resistance to wearing is lower than that of the tampon which is inserted into the vagina.

An example of interlabial pads described above, the labial sanitary pad (Patent Laid-Open No. S61-149145), shown in FIG. 2, has been proposed.

The interlabial pad 24 is used in the following state:

The anterior region of the pad 24a is positioned to the front of the body and the posterior region of the pad 24b is positioned to the rear side of the body. Then, the posterior region of the pad 24b is bent along the longitudinal proximal centerline to form a convex undulation which is inserted and supported between the labia by the pinching force of the labia themselves.

The interlabial pad 24 described above reliably absorbs menstrual blood which flows toward the front and rear of the body along the inner walls of the labia or which flows toward the right and left sides of the body along the skin.

However, the interlabial pad does not have effective performance for absorption of menstrual blood which is excreted downward from inside the labia. This is because when menstrual blood flows toward the front and rear of the body along the inner walls of the labia or flows toward the right and left sides of the body along the skin, the flow is relatively slow because of the friction of the skin and the effect of the pubic hair, in addition, the quantity of flow is small. However, when menstrual blood is excreted downward from inside the labia, with a momentary change of the wearer's posture, menstrual blood accumulated in the womb is excreted at once, flowing rapidly and in a large quantity.

Consequently, the interlabial pad described above is intended to absorb menstrual blood flowing downward from inside the labia by only the convex part formed in the posterior region of the pad, which is parallel in the direction of the flow. Therefore, if menstrual blood flows rapidly and in a large quantity, a part of the liquid can flow along the incline of the convex part without being absorbed by the pad, which causes a possibility that menstrual blood may leak out of the pad. In this case, as the interlabial pad is smaller than sanitary napkins, the resulting leak of menstrual blood is a significant problem.

SUMMARY OF THE INVENTION

The present invention has been developed in view of the problems pointed out above. The object of the present invention is to provide an interlabial pad which reliably absorbs menstrual blood which flows down along the inner walls of the labia, rapidly and in a large quantity. (Hereinafter, the "interlabial pad" may be referred to as "pad".)

In order to solve the problems pointed out above, in the interlabial pad according to the present invention, a part of the flat area having absorptive capabilities is raised to form a protruded area. By configuring the ratio between the convex part and the flat area precisely, even when menstrual blood flows down along the incline of the convex part without being absorbed, the liquid is absorbed in the flat area, which will reduce the possibility that menstrual blood may leak out of the pad.

More specifically, the present invention provides the followings:

(1) An interlabial pad for attaching between labia, comprising: a water permeable surface side sheet facing a body side; a water permeable or water impermeable back side sheet facing a garment side; an absorbent body for absorbing body liquid, the absorbent body being enclosed in the water permeable surface side and the water permeable or water impermeable back side, which are bonded together; a flat area having a substantial plane plate shape and a protruded area projecting vertically towards a body side from said flat area along a substantial center line in a longitudinal direction of said flat area, wherein said flat area and said protruded area satisfy Formulas (1) to (3) shown below.

$$1 \leq H_1/H_2 \leq 10 \quad \text{Formula (1)}$$

$$1/3 \leq W_1/W_2 \leq 5/6 \quad \text{Formula (2)}$$

$$1/3 \leq L_1/L_2 \leq 1 \quad \text{Formula (3)}$$

(where, $H_1$: the apparent bulkiness of the protruded area, $H_2$: the apparent bulkiness of the flat area, $W_1$: the apparent maximum width of the protruded area, $W_2$: the apparent maximum width of the flat area, $L_1$: the apparent maximum length of the protruded area, and $L_2$: the apparent maximum length of the flat area.)

As shown in FIGS. 3(a) and 3(b), the interlabial pads of the present invention have convex parts 34b and 44b which protrude vertically from flat areas 34a and 44a toward the body along longitudinal proximal centerlines 36 and 46 of flat areas 34a and 44a (In other words, continuously in the lateral centers of the flat areas 34a and 44a). When the convex parts 34b and 44b of the interlabial pads 34 and 44 are inserted between the labia, the whole pudenda are covered with the flat areas 34a and 44a, which adjoin the lower ends of the protruded areas 34b and 44b, respectively. Thereby, the protruded areas 34b and 44b, which are inserted between the labia, primarily absorb the majority of excreted body fluid such as menstrual blood. In addition, if the protruded areas 34b and 44b cannot absorb all the liquid, the flat areas 34a and 44a covering the pudenda can secondarily absorb the remainder. Thus, menstrual blood, which flows down along the inner walls of the labia, rapidly and in a large quantity can be absorbed by the protruded areas 34b and 44b in combination with the flat areas 34a and 44a.

The interlabial pad of the present invention must be comprised of the flat area and the protruded area as described above, and both the flat and protruded areas must satisfy the requirements below. This is because, if an interlabial pad is comprised of a flat area and a protruded area but the shapes of the areas are not precisely configured, leak of menstrual blood may occur due to gaps between the interlabial pad and the body, the interlabial pad may fall from between the labia or an absorptive capacity of the absorbent body in the interlabial pad is insufficient. In addition, if the shapes of these areas are not configured precisely, as is the case with tampons, the wearers may sense a foreign feeling or discomfort, which makes it difficult to wear the pad in the vagina.

More precisely, first, the following Formula (1) must be satisfied.

$$1 \leq H_1/H_2 \leq 10 \quad \text{Formula (1)}$$

(where, $H_1$: the apparent bulkiness of the protruded area, $H_2$: the apparent bulkiness of the flat area)

If the ratio of the apparent bulkiness $H_1/H_2$ is less than 1, the rigidity of the flat area, which covers the pudenda, is so high that the wearers may sense a foreign feeling or discomfort in wearing the pad. On the other hand, if the ratio of the apparent bulkiness $H_1/H_2$ is more than 10, the volume of the flat area to absorb menstrual blood which cannot be completely absorbed in the protruded area is so low that leak of menstrual blood may occur.

Second, the following Formula (2) must be satisfied.

$$1/3 \leq W_1/W_2 \leq 5/6 \quad \text{Formula (2)}$$

(where $W_1$: the apparent maximum width of the protruded area, $W_2$: the apparent maximum width of the flat area)

If the ratio of the apparent maximum width $W_1/W_2$ is less than 1/3, the flat area is larger than required. This may cause the wearer to sense a foreign feeling or discomfort in wearing the pad. In addition, the wearer's femoral region (inside of the thighs) and the sides of the interlabial pad or the side of the interlabial pad facing the clothing and the underwear may come into contact with each other. If the friction caused by the contact 2 increases, there is a possibility that the pad may fall from between the labia. On the other hand, if the ratio of the apparent maximum width $W_1/W_2$ is more than 5/6, the flat area is too narrow to cover all of the pudenda in lateral directions. Therefore, the area to absorb menstrual blood which cannot be completely absorbed in the protruded area is so small that leak of menstrual blood may occur.

Third, the following Formula (3) must be satisfied $$1/3 \leq L_1/L_2 \leq 1 \quad \text{Formula (3)}$$

(where $L_1$: the apparent maximum length of the protruded area, $L_2$: the apparent maximum length of the flat area)

If the ratio of the apparent maximum length $L_1/L_2$ is less than 1/3, because not only is the area where the side of the pad facing the clothing and the underwear are in contact with each other longer than required but also the area where the posterior region of the flat area and the buttocks are in contact with each other is increased, the possibility that the pad may fall from between the labia will be increased. On the other hand, if the ratio of the apparent maximum length $L_1/L_2$ is more than 1, the flat area is too short to cover all of the pudenda in the longitudinal direction. Therefore, if menstrual blood is excreted rapidly and in a large quantity, the flat area cannot absorb all of the menstrual blood which cannot be completely absorbed in the protruded area, consequently, the possibility of leak of menstrual blood will be increased.

$L_1/L_2$ of the interlabial pad 44 shown in FIG. 3(b) is approximately 0.5. This pad has an absorptive capability higher than the interlabial pad 34 shown in (a) in FIG. 3(a), which has $L_1/L_2$ of approximately 1, and is suitable for use when menstrual blood is discharged in a large quantity or when the pad cannot often be changed.

In this specification, "bulkiness" refers to the dimension measured in the direction of the projecting protruded area, "width" refers to the dimension measured in the lateral direction of the pad and "length" refers to the dimension measured in the longitudinal direction of the pad.

Also, in this specification, "appearance" means that "bulkiness", "width" and "length" are the shortest distances measured point-to-point. This is particularly defined because distances measured around the undulated surface (in other words, the point-to-point distances measured with the undulations being laid out flat) are sometimes regarded as actual "width" or other dimensions in relation to manufacturing process.

For example, in the case of the interlabial pad 81 shown in FIG. 12, "actual measured width" A of the protruded area 81b is the distance measured around the undulated surface of the protruded area 81b and "actual measured width" B of the protruded area 81b is the total distance measured around the undulated surface of the protruded area 81b and the flat area 81a. On the other hand, the apparent width $W_1$ is the shortest point-to-point distance between both ends of the protruded area 81b and the apparent width $W_2$ is the shortest point-to-point distance between both ends of the flat area 81a. The same thing can be said with bulkiness and length.

(2) The interlabial pad according to (1), wherein $H_1$ in said Formula (1) is 5 to 30 mm, $W_1$ in said Formula (2) is 2 to 30 mm, $L_1$ in said Formula (3) is 20 to 150 mm.

$H_1$ in the above Formula (1) is preferable to be 5 to 30 mm, and more preferable to be 10 to 25 mm. If $H_1$ is smaller than this range, the contact area between the inner walls of the labia and the protruded area is reduced, resulting in the possibility that the pad may fall from between the labia. On the other hand, if $H_1$ is larger than this range, the bulkiness is too high for the depth of the labia, resulting in the possibility of leak of menstrual blood caused by gaps between the surface of the flat area and the pudenda.

$W_1$ in the above Formula (2) is preferable to be 2 to 30 mm, and more preferable to be 5 to 20 mm. If $W_1$ is smaller than this range, the protruded area cannot have enough contact area or volume to be held between the labia, resulting in the possibility that the pad may fall from between the labia. On the other hand, if $W_1$ is larger than this range, the rigidity of the protruded area is so high that it is difficult to insert the pad easily between the labia or that the wearer may sense a foreign feeling or discomfort in wearing the pad.

$L_1$ in the above Formula (3) is preferable to be 20 to 150 mm, more preferable to be 30 to 110 mm, and particularly preferable to be 50 to 100 mm. If $L_1$ is smaller than this range, the contact area or volume the protruded area is not sufficient to be held between the labia, resulting in the possibility that the pad may fall from between the labia. On the other hand, if $L_1$ is larger than this range, the rigidity of the protruded area is so high that it is difficult to insert the pad easily between the labia or that the wearer may sense a foreign feeling or discomfort in wearing the pad.

(3) The interlabial pad according to (1) or (2), wherein a first absorbent body is folded in a mountain fold and enclosed in said protruded area towards the body side, a hollow part is provided on the garment side of said protruded area.

"In a mountain fold" of the present invention does not mean that a protruded area 54b is completely filled up with an absorbent body 53 as shown in FIG. 4(a), but means that a hollow space 57 is formed inside the side of the protruded area 54b facing the clothing (that is, the lower part of the convex) as shown in FIG. 4(b). This is not limited to folding an absorbent body 53b to form a ridge as shown in FIG. 4(c), but includes various shapes made by forming the absorbent body 53 to have a hollow space 57 formed inside the side of the protruded area 54b facing the clothing (that is, the lower part of the convex), such as an inverted U or V-shape, as shown in FIG. 4(b). The hollow space allows the pad to change in form to follow the change in form of the labia, which makes the pad flexible and prevents the foreign feeling or discomfort in wearing the pad.

(4) The interlabial pad according to (3), wherein a water permeable inner sheet is provided on the garment side surface of said first absorbent body formed in a folded shape, and said inner sheet and said surface side sheet are bonded so as to enclose said first absorbent body therebetween.

The hollow part in the protruded area, in addition to being effective for improving the fitting performance of the pad as described above, can also be used as a space for inserting and holding a finger when wearing the pad (a space for finger insertion).

In this case, as shown in FIG. 4(c), when a water permeable inner sheet 58 is arranged on a surface of the garment side of the first absorbent body 53b, it is sanitarily preferable since the finger and the fabric of the absorbent body do not touch each other, and further, there is an advantage such that when the finger is inserted while feeling the inner sheet 58 with the finger pad, the wearing point of the pad can easily be detected.

In addition, since the flat area 54a is scarcely buried between labia when wearing the pad, it is made easy to insert only the protruded area 54b of the pad. That is, since inserting the protruded area 54b between labia into a correct position can be done by the will of the wearer, menstrual blood leaks can surely be prevented, and further, the danger of the pad slipping off the labia is decreased.

(5) The interlabial pad according to any one of (1) through (4), wherein said first absorbent body enclosed in said protruded area and a second absorbent body enclosed in said flat area are formed of a single absorbent body sheet.

As shown in FIG. 5, the first absorbent body (absorbent body enclosed in the protruded area) and the second absorbent body (absorbent body enclosed in the flat area) may also be formed as a continuous single absorbent body 53c. By making a structure like this, the first and second absorbent bodies are not separated, so that no gap is generated between both, and the absorbed menstrual blood moves smoothly from the first absorbent body to the second absorbent body. Accordingly, it is also possible to cope with a fast-moving, large-volume menstrual blood.

(6) The interlabial pad according to any one of (1) through (5), comprising a second protruded area projecting vertically towards a garment side from said flat area along the substantial center line in the longitudinal direction of said flat area.

As shown in FIG. 6, by providing a second protruded area 59 on the garment side in addition to the body side of the flat area 54a, capacity of the absorbent body can be increased substantially. As a result, even a fast-moving, large-volume menstrual blood can be handled, and, even if the pad is used for a long time, danger of menstrual blood leaks due to overflow is reduced. Further, since the second protruded area 59 protrudes to the garment side, the pad can be pinched with fingers when wearing, facilitating wearing the pad.

(7) The interlabial pad according to (6), wherein a third absorbent body is folded and enclosed in said second protruded area towards the garment side, a hollow part is provided in the body side of said second protruded area.

As shown in FIG. 7, when a hollow part 61 is formed in the second protruded area 59, so that stiffness of an absorbent body 60 is decreased for easy deformation even by a light load, the second protruded area 59 is flattened in the right-left direction of the body by a pressure from the garment when wearing the pad. Accordingly, an advantage is that presence of the pad cannot easily be noticed (seen) from outside clothes. Also, since stiffness of the second protruded area 59 is low, friction drag with the garment is decreased as well as the danger of the pad slipping off the labia is decreased.

(8) The interlabial pad according to any one of (1) through (7), wherein at least fibers for forming said water permeable surface side sheet in said protruded area and that of said first absorbent body are oriented in a lateral direction of said interlabial pad.

By arranging fibers composing the surface side sheet and the first absorbent body in the width direction, the absorbed menstrual blood can easily move in the arrangement direction of the fiber layer, namely in the lateral direction of the body, and the menstrual blood can easily be moved from the first absorbent body to the second absorbent body. Additionally, as indicated by the expression "at least," besides the surface side sheet and the first absorbent body, the arrangement of fibers composing other members (such as the second absorbent body, the third absorbent body, the inner sheet and the like) in the width direction of the pad are also included in the scope of the present invention.

(9) The interlabial pad according to any one from (1) to (8), wherein an adhesion part is provided on the body side surface of said flat area.

As shown in FIGS. 8(a) and 8(b), by forming an adhesive portion 62 in the surface side sheet 51 like this, the pad can be adhered between labia or to the pudenda more firmly, and generation of a gap between the pad and the body, even by a sudden change in posture of the wearer, can be prevented. Accordingly, the wearer can act freely, without having any restrictions on her actions.

The "adhesive part" can be formed by applying the adhesive to the surface side sheet. The adhesive agent available for the present invention may be exemplified by a gel adhesive made of water-soluble polymer, crosslinking agent, plasticizer and moisture. More specifically, examples of the water soluble polymer used herein are gelatin, sodium polyacrylate, polyvinyl alcohol, and carboxymethyl cellulose. Examples of the crosslinking agent are water-soluble metallic salt such as calcium chloride and magnesium sulfate and examples of the plasticizer are glycerol, wax, and paraffin.

As other adhesive agent, a pressure sensitive hot melt adhesive can be also used. The pressure sensitive hot melt is mainly formed of synthetic rubber resin such as styrene-isoprene-styrene block copolymer (SIS), styrene-butadiene-styrene block copolymer (SBS), styrene-ethylene-butadiene-styrene block copolymer (SEBS), and styrene-ethylene-propylene-styrene block copolymer (SEPS). The pressure sensitive hot melt adhesive can be obtained by fusing and mixing an adhesion additive such as terpene resin or rosin resin and a plasticizer such as wax to the pressure sensitive hot melt.

Also, a silicone adhesive agent can be used as other adhesive. An example of the silicone adhesive is a mixture obtained by mixing a crosslinking agent such as metallic salt of platinum, molybdenum, or antimony and a plasticizer such as ester wax, glycerin, or machine oil.

Like this, there are many kinds of adhesive agents for forming the adhesive part, but if the application stability is taken into consideration, the pressure sensitive hot melt is preferable. More specifically, it is an adhesive agent prepared by fusing and mixing 15 to 25 weight % of SEBS, 15 to 35 weight % of plasticizer, and 40 to 70 weight % of adhesive adder. Also, according to circumstances, it is possible to add antioxidant, antifluorescent or the like within the range of 0.1 to 1.0 weight % to the pressure sensitive hot melt.

(10) The interlabial pad according to any one of (1) through (9), wherein the interlabial pad is used together with a sanitary napkin.

There are some sanitary napkin (henceforth referred to simply as "napkin") users who use several pieces of napkins layered together when there is a large quantity of menstrual blood. However, there cause problems that they cause uncomfortable feeling such as stiffness, and their presence is noticeable from the outside of the garment. Further, layered napkins cover portions other than the neighborhood of ostium vaginae where the layered use is unnecessary cause a rash or a sweat. However, using a pad and a napkin, the sanitary products are layered only on the labia and its periphery so that above-mentioned problems can be avoided. Furthermore, it is possible to change only the pad according to the present invention without changing the napkin. Therefore, there is no need for the wearer to carry around the sanitary napkins which are large enough to be noticed. The sanitary napkins herein are not only the napkins which are sold for absorbing menstrual blood but may also include absorption sheets for vaginal discharge.

(11) The interlabial pad according to any one of (1) through (10), wherein: on the garment side of said back side sheet, a mini sheet piece is provided bonding one or more bonding areas in each side in the longitudinal direction of said back side sheet and one or more unbending areas in the lateral direction of said back side sheet; and at least one of said one or two unbonding areas, between said mini sheet piece and said back side sheet, forms a finger insertion opening which can directly secure a fingerbreadth opening in the surface direction of said back side sheet.

In FIGS. 9(a) and 9(b), in a lateral direction of the back face side sheet 52, at least one of both sleeve portions of the mini sheet piece 64 is not bonded with the back face side sheet 52 surface. Thereby the opening is formed between one sleeve side of the mini sheet piece 64 which is in a non-bonding condition and the back face side sheet 52 to form the finger insertion opening 53 which is capable of inserting the finger.

In a longitudinal direction of the back face side sheet 52, the mini sheet piece 64 is connected with only both lateral sides of the back face side sheet 52 and is not bonded to (adhered) the inside thereof. Therefore, the mini sheet piece 64 is provided from one lateral side of the back face side sheet 52 to the other lateral side thereof in a state of extending over. Therefore, at such a portion such extending over from one lateral side to the other, penetrating or non-penetrating space (space for inserting the finger) is formed. Such space can be inserted with the finger to keep it therein.

The word "finger breadth" in this specification does not mean the thickness of the finger but specifically means the width direction of the finger in the spread direction of the nail. The opening of the finger breadth means a sufficient size to insert the finger.

The opening of the finger breadth is directly kept in a direction of the back face side sheet surface. This means that when the finger is inserted into the pad normally to wear the pad, (the ball of a finger is directed to the garment face side of the back face side sheet and is inserted to maintain the condition), the pad of itself is formed to be adequate for inserting the finger primarily. Therefore, the following case is except from above described example, such that the opening for the finger breadth is kept in a surface direction by rotating the finger after the person inserts the finger and the opening for the finger breadth is formed on the back face side sheet surface side secondarily.

As described hereinbefore, in the pad provided with the mini sheet piece, the finger is inserted into the opening through, thereby the pad can be kept and fixed at the finger for the time being. In this case, the finger insertion opening is formed to be the opening for the finger breadth, and the flat-shaped finger tip is prevented from directing to the different direction in respect of the back face side sheet and is inserted to contact with the back face side sheet surface naturally. That is, since the finger insertion opening has a wide shape in a direction of the back face side sheet surface in accordance with the shape of the finger tip of the person to wear, it is intended that the user acts to determine the direction to which the finger is inserted by detecting a fix point of the pad by the finger tip. Thereby for attaching the pad between labia where the person is difficult to confirm by eyes, the pad can be attached at the adequate position by correctly holding a correct attachment point.

Further in the pad of the present invention, not only the peripheral edge portion of the pad but also the neighborhood of the peripheral edge portion to where the mini sheet piece can be connected are included in the side portion in the longitudinal direction of the back face side sheet.

(12) The interlabial pad according to any one of (1) through (11), wherein the interlabial pad is a pad for incontinence of urine.

According to the interlabial pad of the present invention, the pad can be used for a pad for absorbing incontinence of urine. That is, ostium vaginae where the menstrual blood is discharged and a urethral meatus where urine is discharged locate between labia, and the interlabial pad of the present invention to be used between labia can absorb urine also.

As described hereinbefore, the pad of the present invention can absorb urine around labia, especially around the urethral meatus and is useful for the absorbing pad for incontinence, especially for a light incontinence.

(13) The interlabial pad according to any one of (1) through (11), wherein said interlabial pad is an interlabial pad for absorbing vaginal discharge.

In accordance with the present invention, the interlabial pad can be used for the pad of absorbing the vaginal discharge. That is, the interlabial pad is used between labia and can absorb the excretion other than the menstrual blood from ostium vaginae such as the vaginal discharge.

As described above, the pad can absorb the vaginal discharge in order to decrease the discomfort for the person, and is useful even for the user who is not menstruating.

(14) A wrapping body, comprising: an interlabial pad according to any one of (1) through (13); and a wrapping container for individually wrapping the interlabial pad wherein the interlabial pad is enclosed in the wrapping container.

The interlabial pad is packaged individually and the pad can be carried one by one (every individual package). As compared with a plurality of pads enclosed in one wrapping container, the pad is kept sanitarily, can be easily carried and can be treated simply.

(15) A wrapping body comprising: an interlabial pad according to any one of (1) through (13); a wrapping container, having a break seal opening, for individually wrapping the interlabial pad, wherein the interlabial pad is enclosed in the wrapping container; wherein said interlabial pad is wrapped in said wrapping container so that a finger insertion opening opens towards said opening part.

As illustrated in FIG. 13, "to provide the finger insertion opening toward the break seal opening of the wrapping body", means that when the wrapping body 92 is opened, the mini sheet piece 95 and further the opening 96 for inserting the finger which is formed by the sheet piece appear and the finger can be rapidly inserted into the opening 96. For example, as illustrated in FIG. 13, the wrapping body 92 can be opened by opening the upper surface sheet 91a of the wrapping container 91 to the rear side of the drawing. The finger insertion opening 96 appears at the opening of the wrapping body toward the break seal opening. Therefore the user can insert the finger rapidly into the opening 96.

In this case, for example, a structure that allows the wrapping body 92 to be opened only in a certain direction, or, as shown in FIG. 13, addition of a mark 97 showing the opening direction in the wrapping container 91, is preferable. By applying a composition like this, since the opening direction and the direction of finger insertion are arranged along the same direction as well as the finger insertion port 96 is oriented to the wearer, the wearer can insert her finger into the finger insertion port 96 more smoothly.

(16) The wrapping body according to (15), wherein said interlabial pad is enclosed in said wrapping container so that said mini sheet piece is folded towards the clothing direction along the substantial center line in the longitudinal direction of said interlabial pad.

The phrase "so that it is folded in a mountain fold toward the garment side" includes not only cases where it is completely folded and the fold is on the garment side, but also means cases as shown in FIG. 14 where it is bended toward the garment side. By thus enclosing the interlabial pad 104 in the wrapping container 101, the folded finger insertion opening 106 spontaneously opens upon opening of the wrapping container 101, allowing the wearer to easily identify the place to insert the finger, and makes application of the interlabial pad faster and easier.

In this embodiment, provided that the mini-sheet piece is "folded in a mountain fold", it is not required for the entire interlabial pad to be "folded in a mountain fold". Therefore, for example, other than the wrapping body 102 enclosing the entire interlabial pad 104 as shown in FIG. 14, wherein said interlabial pad is folded "in a mountain" fold and enclosed inside wrapping container 101, only the mini-sheet piece 105 may be folded "in a mountain fold" as shown in FIG. 15. On the other hand, it may be a wrapping body 102, wherein the main part of the interlabial pad 104 is folded toward the garment side in a valley fold and enclosed inside a wrapping container 101.

Additionally, the method of opening the wrapping container is not particularly limited, as shown in FIGS. 14 and 15, it may be opened by cutting off the upper end of the wrapping container 101, or else, as shown in FIG. 16, it may be a wrapping container 111 that opens to both sides from the upper end (in the method of the so called "double doors").

BRIEF DESCRIPTION OF THE DRAWINGS

FIGS. 1(a) and 1(b) are drawings showing the composition of an interlabial pad according to the present invention, FIG. 1(b) is a plan view, and FIG. 1(a) is a cross-section of FIG. 1(b) along the line A-A'.

FIGS. 3a-b illustrate perspective views showing the composition of the interlabial pad according to the present invention.

FIGS. 4a-c illustrate perspective views showing a cross-section of the interlabial pad according to the present invention.

FIGS. 8(a) and 8(b) are drawings showing the composition of an interlabial pad according to the present invention, FIG. 8(b) is a plan view, and FIG. 8(a) is a cross-section of FIG. 8(b) along the line A-A'.

FIGS. 9a-b illustrate perspective views showing a cross-section of the interlabial pad according to the present invention.

BEST MODE OF CARRYING OUT THE INVENTION

Figure 2:
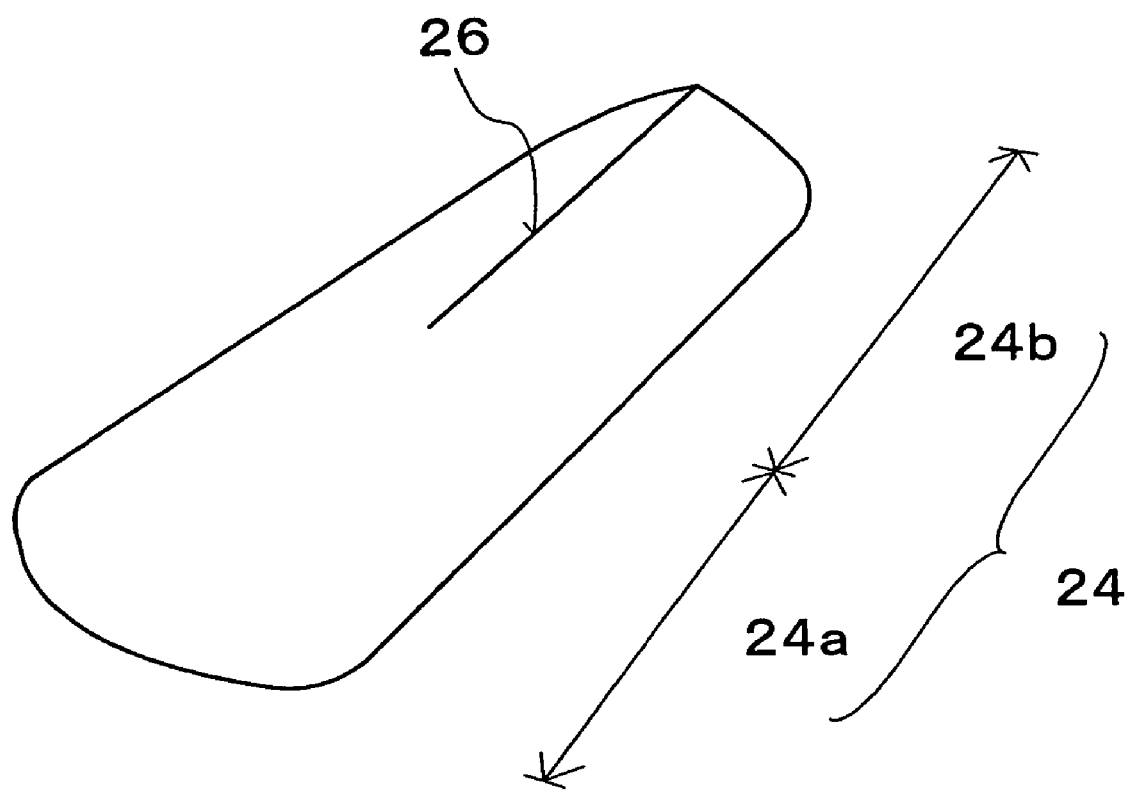
FIG. 2 is a perspective view showing the composition of a conventional interlabial pad.
Figure 5:
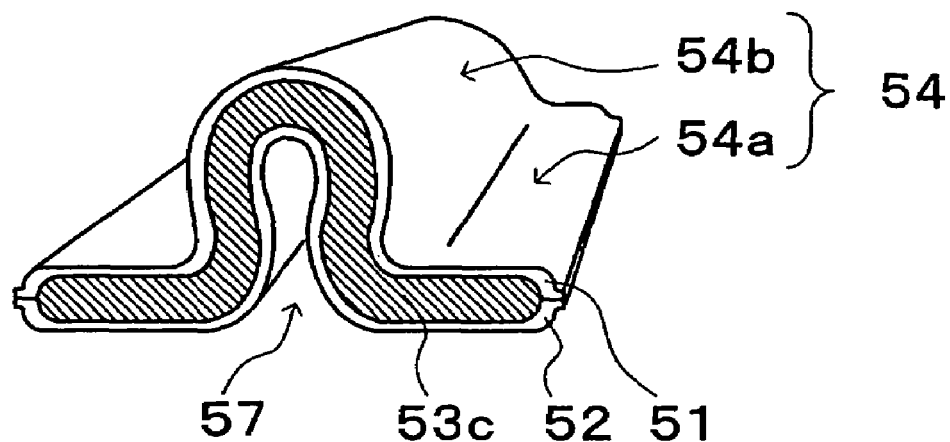
FIG. 5 is a perspective view showing a cross-section of the interlabial pad according to the present invention.
Figure 6:
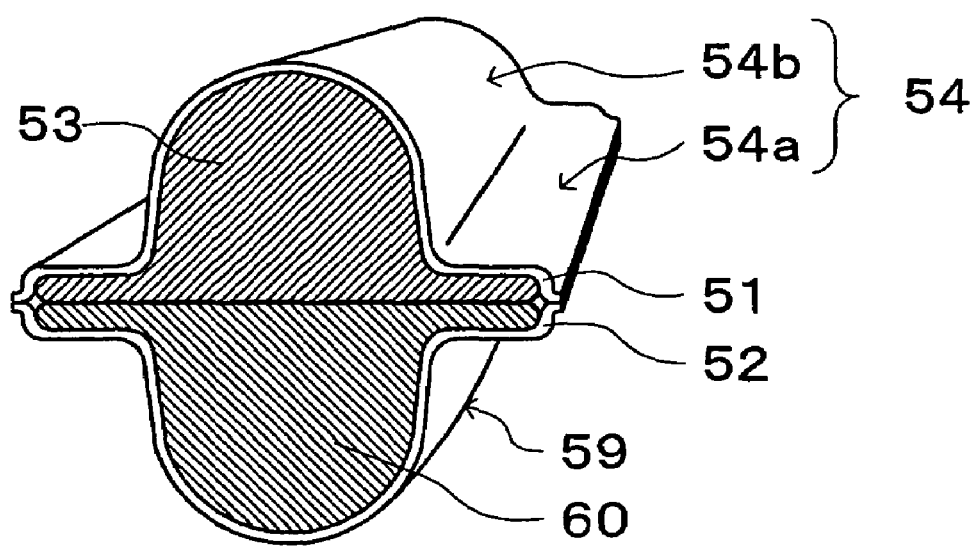
FIG. 6 is a perspective view showing a cross-section of the interlabial pad according to the present invention.
Figure 7:
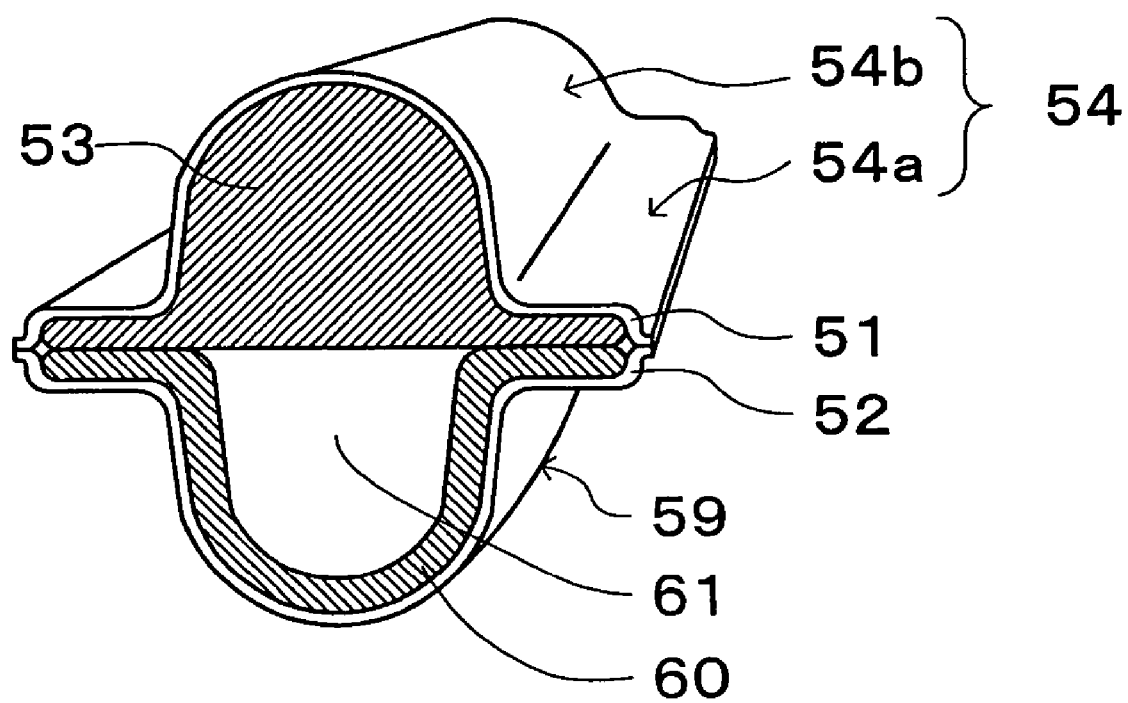
FIG. 7 is a perspective view showing a cross-section of the interlabial pad according to the present invention.

Preferable embodiments of the present invention are described by referencing the drawings.

FIGS. 1(a) and (b) are drawings showing an interlabial pad according to the present invention, FIG. 1(b) is a plan view, and FIG. 1(a) is a cross-section of FIG. 1(b) along the line A-A'.

[(A)Basic Composition of the Interlabial Pad]

As shown in FIG. 1, a basic interlabial pad 14 according to the present invention (henceforth referred to simply as "pad") is composed of a flat area 14a and an protruded area 14b. And, a water permeable surface side sheet 11, facing the body side, a water permeable back face side sheet 12, facing the garment side, and an absorbent body 13 are provided, where the surface side sheet 11 and the back face side sheet 12 are unified at a flange part 15 by heat embossing and/or hot melt bonding so as to enclose the absorbent body 13.

When bonding flange parts of the surface side sheet 11 and the back face side sheet 12, it is preferable to not include the absorbent body 13. Because, if the absorbent body 13 is caught between the bonded parts, the pad 14 is hardened at the flange part 15 and foreign feeling and discomfort may occur during wearing. To surely prevent the absorbent body 13 from being caught between said bonded parts, for example, the surface side sheet 11 and the back face side sheet 12 are bonded to form a bag shape, leaving an opening at a part, and the absorbent body 13 is packed into the bag part. Additionally, the absorbent body 13 can be dimensionally the same as the pad 14, but to surely prevent the absorbent body 13 from being caught between said bonded parts, the absorbent body 13 may be a little smaller than the pad 14 so that a clearance of 2-10 mm can be secured from the outer flange of the pad 14.

It is not limited to the specific whole form of the interlabial pad 14 and the form may be adequate to attach to labia. For example an elliptic type, ovoid, a gourd-shape or a drop-shape and the like will be eligible.

[Surface Side Sheet]

As the water permeable surface side sheet, sheet-shaped materials having a structure to permeate liquid, such as a woven fabric, a nonwoven fabric and a porous plastic, can be used without any particular restrictions. As woven and nonwoven fabrics, both natural and chemical fabrics can be used. For natural fabrics, cellulose such as crushed pulp, cotton, can be named. For chemical fabrics, regenerated cellulose, such as rayon and fibril rayon, semisynthetic cellulose, such as acetate and triacetate, and hydrophilic-treated thermoplastic hydrophobic fibers can be named. As said thermoplastic hydrophobic fibers, single fiber, such as polyethylene (PE), polypropylene (PP) and polyethylene telephthalate (PET), graft-polymerized fibers of PE and PP, and compound fibers with PP or PET cores and PE sheaths can be named.

Especially for nonwoven fabrics, web forming can be done by a dry method (carding, spun bonding, melt-blown, air-laid and the like) or by the wet method, either independently or in combination. Examples of bonding methods are thermal bonding, needle punching and chemical bonding, but not especially limited to these methods. Further, a sheet-formed spun lace by the columnar water flow method is also available.

Examples of perforated plastic sheets used are an air sheet of thermoplastic resin such as polyethylene (PE), polypropylene (PP), and polyethylene terephthalate (PET), and a perforated foamed material. Also, it is preferable to use it by making it milky by mixing a filler made of titanium oxide, calcium carbonate and the like within the range of 0.5 to 10 weight % if necessary. A perforated film obtained by perforation, thermal embossing, machine processing or the like on a thermoplastic film may also be used. Furthermore, a composite sheet of the perforated film and nonwoven fabric may also be used.

Among the materials, considering the liquid mobility from the inner face of the labia, chemical stimulation by an activator, and adhesion with the inner wall of the labia, it is preferable to laminate rayon with 1.1 to 4.4 dtex fineness and 7 to 51 mm fiber length by 40 to 80% of a total specific weight per unit area on the body surface side, and to laminate a mixture of rayon with 1.1 to 4.4 dtex fineness and 7 to 51 mm fiber length by 14 to 42% of a total specific weight per unit area and PET with 1.1 to 4.4 dtex fineness and 7 to 51 mm fiber length by 6 to 18% of a total specific weight per unit area on the garment face side. After laminating them so that the total specific weight per unit area of the two layers becomes 20 to 60 g/m², the fibers are entangled by water-flow interlacing treatment and then dried to prepare spun lace nonwoven fabric with the thickness of 0.13 to 0.50 mm. The spun lace nonwoven prepared as described is preferable. At this time, by mixing PET on the garment side, bulkiness can be easily maintained even if the water permeable sheet becomes wet. Therefore, adhesion between the inner wall of the labia can be maintained.

[Absorbent Body]

The absorbent body may be capable of keeping and absorbing a liquid (the menstrual blood) and preferably may be bulkiness, may not be difficult to lose the shape and may be less chemical stimulation. For the material of the absorbent body, cellulose (ground pulp, cotton and the like), a regenerated cellulose (a viscose rayon and a fibril rayon and the like), a semi synthetic cellulose (acetate and triacetate and the like), a particle water-absorbent polymer, a fiber-type water-absorbent polymer, a chemical fiber (a heat flexible hydrophobic chemical fiber which is treated in hydrophilic and the like), chemical bonded air laid pulp and a hydrophobic resin can be used in single or can be mixed.

Also, cellulose foam, a continuous foam and the like of synthetic resin can be also used as the absorbent body. Furthermore, an absorbent body obtained by grinding and molding the above-described sheet and the foam can be used.

It is preferable for the absorbent body, although any material can be used as long as it is capable of absorbing and holding liquid (body fluid), to be bulky, hard-to-be deformed, less chemically stimulant, and highly flexible to fit into the labia. Specifically, a nonwoven sheet in which, 50 to 150 g/m² of pulp selected from the range of the fiber length of 1 to 10 mm is laminated on the garment face side and, on the body face side, 150 to 250 g/m² of a mixture obtained by mixing 60 to 90% of rayon with 1.1 to 4.4 dtex fineness and 20 to 51 mm fiber length with 40 to 10% of natural cotton by this mixing ratio is laminated, which then to be formed into a sheet by dotted embossing to have 2 to 10 mm bulkiness, and more preferable to have 3 to 5 mm bulkiness. Thereby, liquid can be easily transmitted from the body face side to the garment face side resulting in the improvement of the absorbing and holding capacity. Furthermore, by providing a mesh spun lace nonwoven fabric of rayon with 1.1 to 4.4 dtex fineness and 25 to 51 mm fiber length by a specific weight per unit area of 15 to 40 g/m², the liquid transmitted from the body face side can be dispersed by the mesh spun lace to be induced to almost all over the region of the pulp layer. Therefore, more liquid can be effectively absorbed.

[Back Face Side Sheet]

In case of using the water permeability material for the back face side sheet, the same material, which is used for the surface side sheet, is eligible. In this case, it prefers to use the pad together with a sanitary napkin (a pad used together with the sanitary napkin).

Further if non-water permeability material is used for back face side sheet, the menstrual blood, which is kept in the absorbent body, is prevented from a leak out of the interlabial pad. Furthermore the pad can be comprised of water vapor permeability material, thereby in wearing the pad, the sweat and the discomfort can be decreased.

When adopting an impermeable material, an impermeable film mainly made of PE, PP or the like, a breathing resin film, and a material in which a breathing resin film is bonded to the back side of a nonwoven fabric such as a spun bond or spun lace on which water-repellent processing is performed can be used. When adopting an impermeable material, considering the degree of softness by which the wear feeling is not influenced, for example, a film obtained by a specific weight per unit area of 15 to 30 g/m² mainly using LDPE (low density polyethylene) may be used. It is more preferable to reduce the contact ratio to decrease the friction drag value by embossing the above-described film to provide convex-shaped projections in order to, when the pad is worn between the labia, decrease the risk of the interlabial pad from being fallen off from the labia due to the high friction caused by the contact between the water impermeable sheets, or with a pad used together, an underwear or the like.

[Mini Sheet Piece]

A material used for the mini sheet piece is selected in consideration of having an enough strength against a damage by the inserted finger, preferably it can be selected individually from one laminated a sheet-typed nonwoven fabric, an elastic and expand nonwoven fabric, a film, a foam film, an elastic and expand film, a foam sheet, a tissue paper and the like. A specific example is a film of 15 to 30 μm thickness having an LDPE resin as the main component.

Also, the mini sheet piece can be prepared to have the tone of color, design, chroma which are different from those of the back side sheet by coloring or printing a design or the like in order for the wearer to be able to easily discriminate the mini sheet piece.

In order to effectively use the interlabial pad according to the present invention, it is also effective to prepare the above-described mini sheet piece to have a characteristic of stretching or elastic dilation in the lateral direction of the back side sheet regardless of the finger size of the wearer.

In order for the mini sheet piece to have a stretching characteristic, a stretching spun bond nonwoven fabric can be used in which the stress is 0.1 to 0.5 N/25 mm at the time of 5% stretching when being stretched at a constant speed by a stretching speed of 100 m/minute with a grip interval of 100 mm. Also, in order for the mini sheet piece to have an elastic dilation characteristic, a fiber sheet or film sheet using thermoplastic elastomer resin may be used. Also, the elastic dilation material such as the thermoplastic elastomer resin or natural rubber may be used alone or may be combined with a non-elastic dilation material to be used.

[Adhesive Portion]

Examples of the manner in which the adhesive portion is applied are in the form of whole surface application or in dots, mesh, or lines. The position of the adhesive portion is not specifically limited as long as it enables fixing of the pad to the body. However, specifically considering the existence of the pubic hair in the area in front of the labia, it is preferable to position the adhesive near both end sides of the interlabial pad in lines with about 1 to 5 mm width.

It is preferable to cover the part where the adhesive is applied with a sheet obtained by coating silicon resin on a tissue paper, which is a generally obtainable separate paper, or a sheet obtained by coating silicon resin on a film. Thereby, damages or separation of the adhesive part can be prevented while being stored.

An example of valuation method of the adhesive strength will be described in detail. The valuation method is to measure the separation force (FIG. 10) and the shearing force (FIG. 11) of the adhesive, using a constant speed expansion tensile tester and a stainless plate 71 having a length of 80 mm and a width 50 mm.

As a preparation for the evaluation test, a test piece of a polyethylene film 72, nearly the same in size with the stainless plate 71, in which an adhesive 73 is applied within the range of 25 mm in width and 50 mm in length is left for 30 minutes at a room temperature of 20° C. beforehand. Subsequently, the polyethylene film 72 is put lightly over a stainless plate 71 so as the adhesive 73 to come in contact with the stainless plate 71, and a 2 kg-roller is applied once (one way only). Then, it is left for 30 minutes at a room temperature of 20° C.

Figure 10:
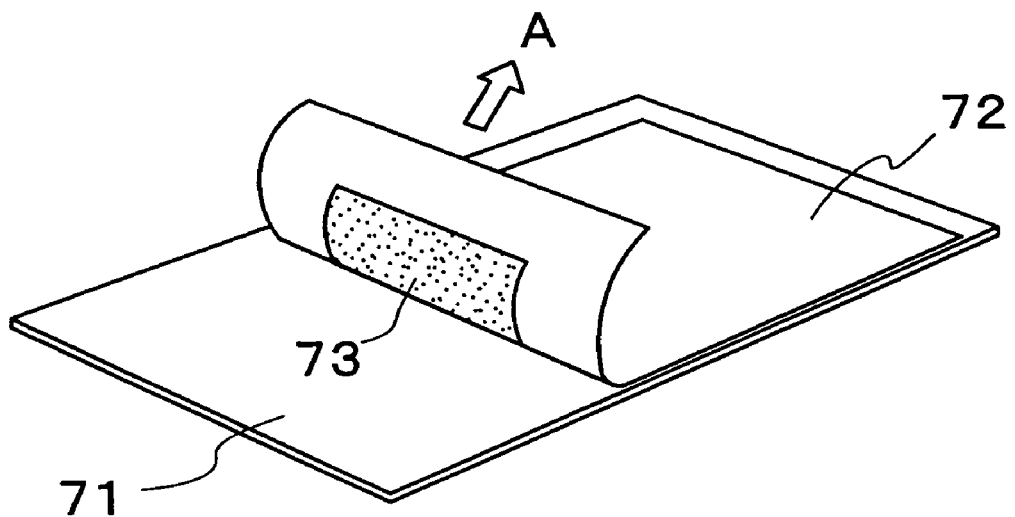
FIG. 10 is a drawing showing the test condition of peeling strength measurement of an adhesive.
Figure 11:
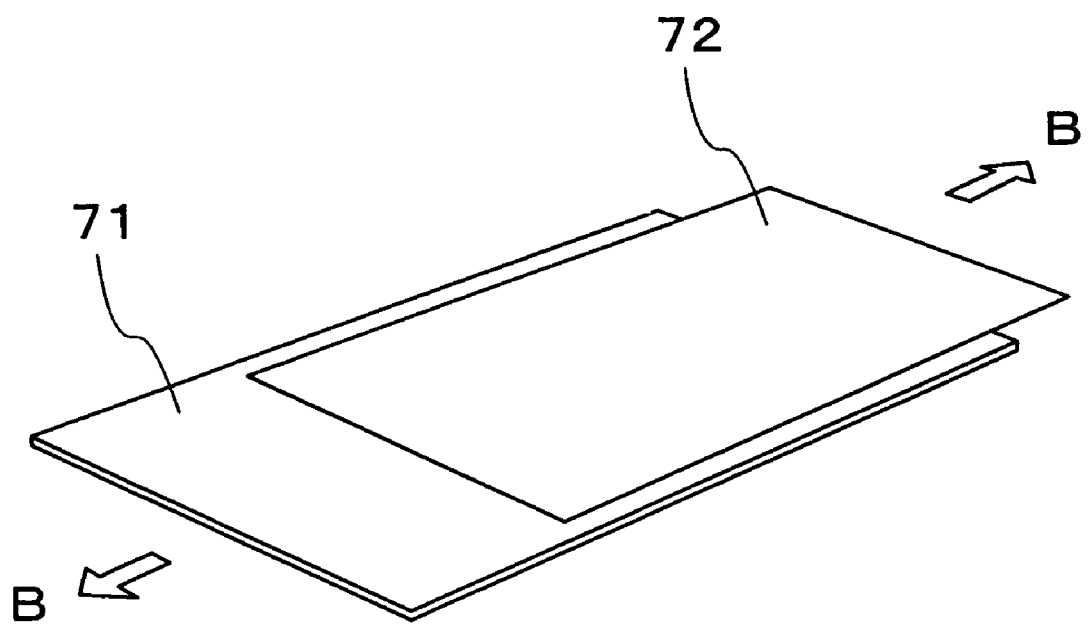
FIG. 11 is a drawing showing the test condition of shear strength measurement of the adhesive.
Figure 12:
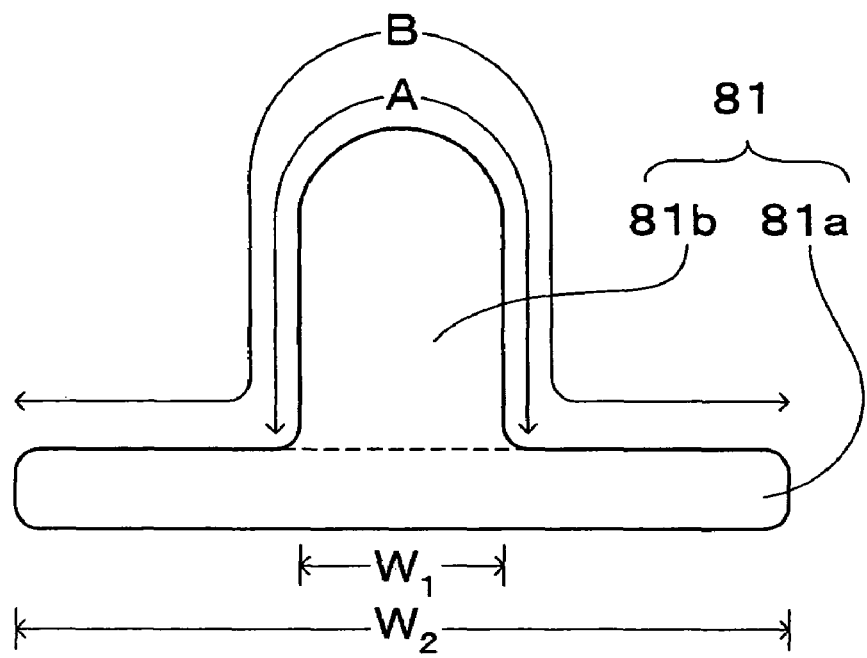
FIG. 12 is an explanatory drawing showing the difference of the "actual width" and the "appearance width" referred to in this specification.
Figure 13:
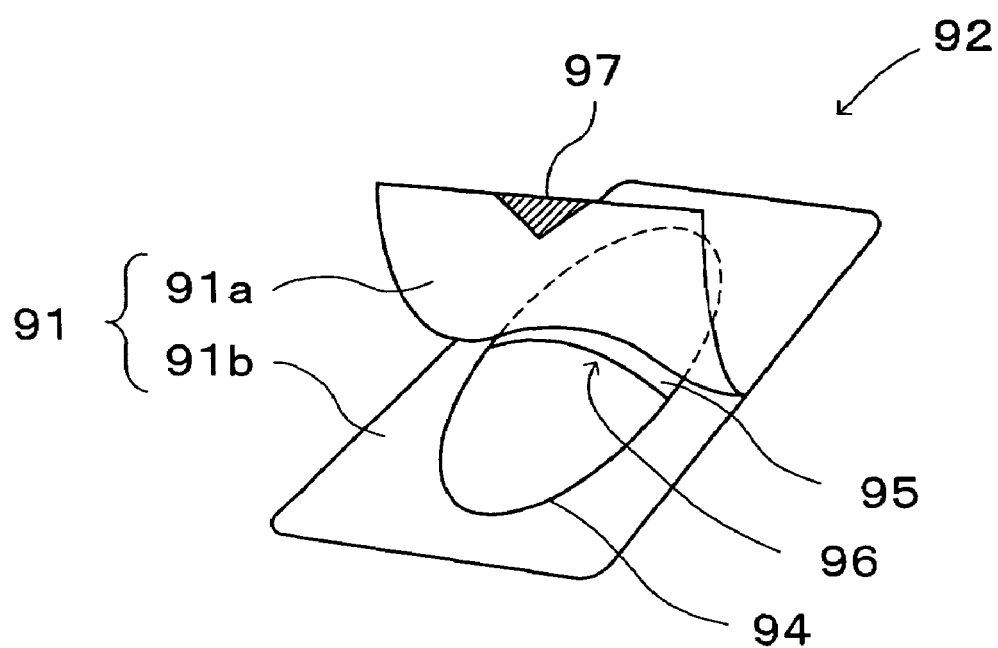
FIG. 13 is a perspective view showing a composition of a wrapping body according to the present invention.
Figure 14:
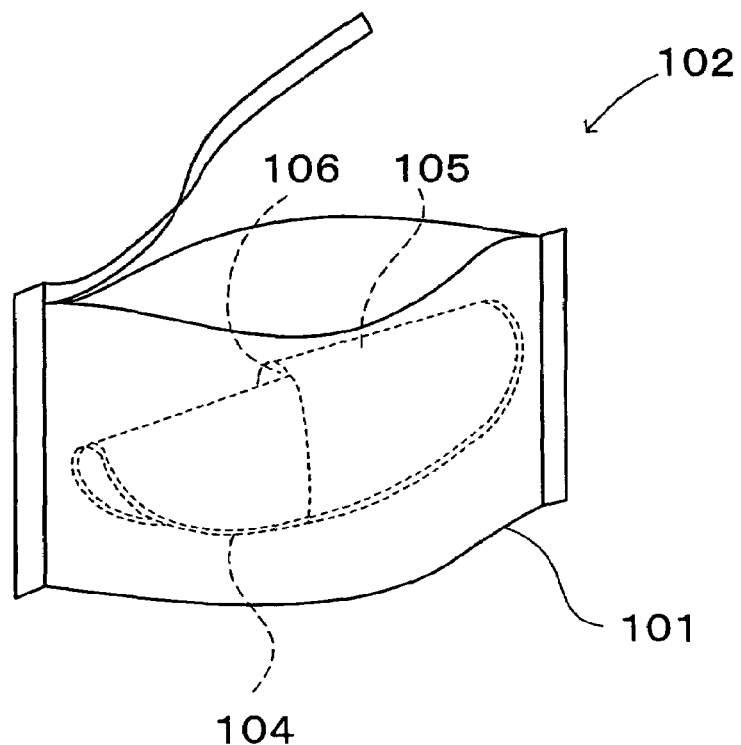
FIG. 14 is a perspective view showing a composition of a wrapping body according to the present invention.
Figure 15:
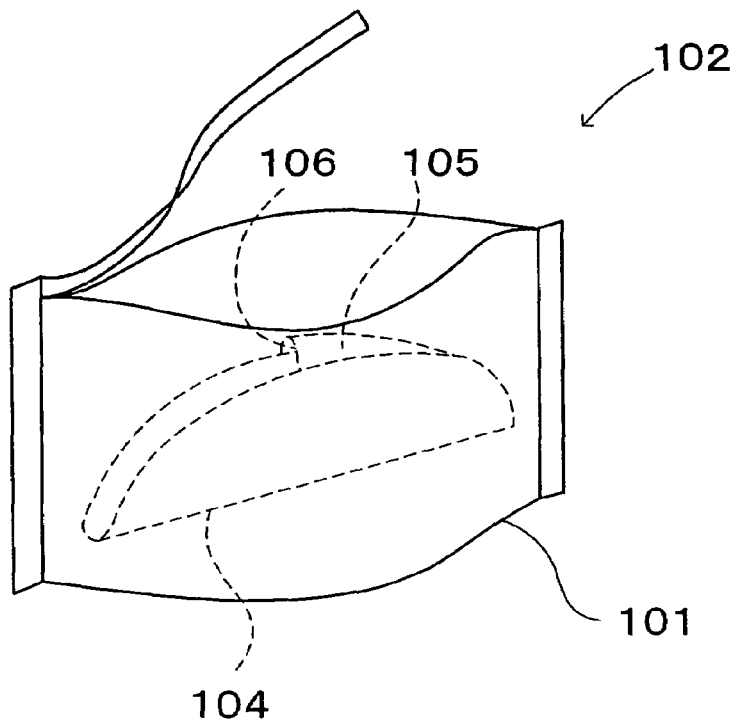
FIG. 15 is a perspective view showing a composition of a wrapping body according to the present invention.
Figure 16:
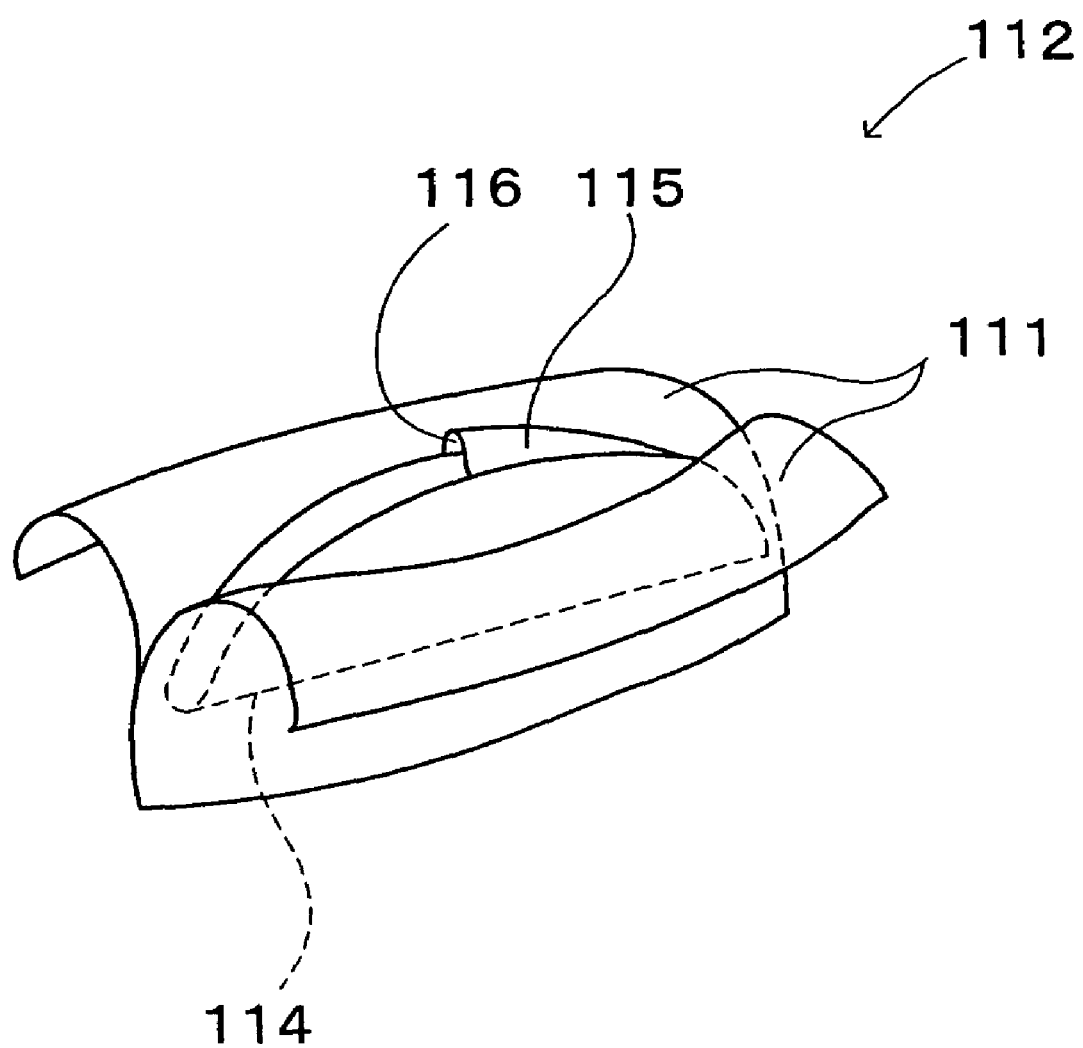
FIG. 16 is a perspective view showing a composition of a wrapping body according to the present invention.

In the separation strength test, a portion of the testpiece of the polyethylene film 72 prepared as above is separated by pulling in the direction of the arrow A shown in FIG. 10, or in the direction of the arrow B, shown in FIG. 11, in the shear strength test. Test conditions are a chuck spacing (clamp spacing) of 70 mm and a pull speed of 100 mm/min.

In the case where the forces are measured by the measurement methods described above, considering the burden imposed on the skin of the wearer, it is preferable that the measurement value of the separation strength be 100 to 2000 mN/25 mm and that of the shear strength be 2900 to 15000 mN/25 mm.

[(B) Structure of the Interlabial Pad Provided with Biodegradability, Water Dispersibility and Water Solubility]

Preferably, the interlabial pad of the present invention is composed of biodegradable material and/or water dispersible material and/or water soluble material. Such an interlabial pad can be flushed by just dropping into the toilet after use, allowing easy and sanitary discard of the interlabial pad, and also can aim to reduce wastes within the toilet.

In this Specification, "biodegradability" means that a substance is decomposed into gas such as carbon dioxide or methane, water, and biomass under anaerobic or aerobic condition according to the natural process under the existence of bacteria represented by actinomycetes and other microbes, and also means that the biodegradability (biodegradable rate and biodegradable degree) of the substance equals to a material naturally generated such as fallen leaves or a synthetic polymer generally recognized having the same biodegradability under the same environment. "Water dispersibility" means the same as water solubility, where there is no effect from the limited amount of water (menstrual blood) upon use, whereas in conditions of large amounts of water or under water flow, the fibers are easily dispersible into at least small pieces which cannot clog the toilet plumbing. "Water solubility" means the property of not being affected by limited amount of water (menstrual blood) upon use, but being soluble in large amounts of water or under a flow of water.

[Surface Side Sheet]

Any of natural fiber and chemical fiber can be used for materials of the water permeable surface side sheet to achieve biodegradability, water dispersibility and water-solubility.

For example of natural fiber, there are cellulose such as a grinding pulp and cotton and air laid pulp and the like which is chemically composed by water-soluble resin. For examples of chemical fiber, there are regenerated cellulose such as rayon, fibril rayon, materials which is hydrophilic treated to the chemical fiber such as PE, PP, PET, ethylene-vinyl acetate copolymer, moreover polylactic acid so-called biodegradable fiber, and polybutylenesuccinate and the like. Further water-soluble carboxymethylcellulose and polyvinyl alcohol are eligible for use. In these materials, it prefers to use biodegradable fiber that are cellulose such as a pulp and cotton, regenerated cellulose such as rayon and the like and polylactic acid.

Materials described hereinbefore can be used independently or be mixed by forming a web or a nonwoven fabric. For web forming biodegradable fabric such as polylactic acid or polybutylene succinate and the like, any of methods such as a dry method (card method, spun bond method, melt blown method, air laid method) and a wetting method, or a combination of a plurality of methods thereof is eligible. For a method of bonding, a thermal bonding, a needle punch bonding, a chemical bonding are eligible, however it is not limited to these method.

Further a spun lace formed in a sheet-shaped by a water flow confounding is eligible.

For an example of a forming method of applying water dispersibility, a method of producing a water dispersible paper which the fiber is formed in the sheet-shaped by a hydrogen bonding of fiber themselves, a method of producing water dispersible paper which fibers are bonded each other into sheet-shaped by water soluble binder or a method of producing water dispersible paper which fibers are confounded into sheet-shaped are eligible.

Preferably a length of fiber in a range from 2 to 51 mm, most preferably in a range from 2 to 10 mm can achieve a good ability of water dispersibility. Further in addition to water dispersibility, preferably fineness (thickness) of fibers is selected from a range of 1.1 to 4.4 dtex for also having strength not to damage the pad in use. Especially in using rayon as a fiber, it prefers to select the fiber having fineness from 1.1 to 3.3 dtex. In case of fineness being less than the value described above, it is possible to achieve water dispersibility, however in a dry condition, water dispersibility is extremely deteriorated by easily becoming fuzz or coming out of fuzz from fibers.

Preferably the amount of the surface side sheet is selected from a specific weight per unit area 20 to 60 g/m². Further it is required that the breaking strength of the surface side sheet is 800 mN/25 mm at least in both vertical and horizontal directions and preferably is from 1000 to 7000 mN/25 mm in consideration of the softness in wearing the pad (the breaking strength of the sheet evaluated from the constant speed extension by a speed testing 100 mm/min in a condition of a knob distance 100 mm).

For further concrete structure of the surface side sheet, a wet forming spun lace nonwoven fabric is eligible, that a rayon having a fineness of 1.1 to 4.4-dtex and a length from 5 to 10 mm and a wood pulp are mixed in a ratio from 90:10 to 70:30 by mass to adjust a specific weight per unit area 25 to 40 g/m², and the thickness from 0.2 to 0.5 mm. In order to substantially improve the water permeability of the menstrual blood or to apply an good image of the menstrual blood permeability, a plurality of holes can be also provided on the sheet in configuration having a hole diameter from 0.5 to 1.5 mm and a rate of hole area (a ratio of opening hole in respect of whole area) from 3 to 20%.

[Absorbent Body]

Same materials having water permeability for the surface side sheet can be used for materials of the absorbent body. Further it is possible to independently use the absorbent body such as alginic acid soda, starch, carboxymethylcelluloce, and the like, particle-typed or fiber-typed super absorbent polymer, or to use a form by mixing these materials above described.

In respect of the structure of the absorbent body, the wood pulp and the like are eligible, that is laminated to a specific weight per unit area 150 to 500 g/m² to enclose into tissue and is adjusted the thickness from 2 to 10 mm by a press device. It is possible to improve the absorption capacity or keeping ability of the menstrual blood by mixing absorbent body such as starch and the like in a ratio from 5 to 30 g/m².

[Back Face Side Sheet]

Examples of the water impermeable material of the back face side sheet are cellulose derivative such as methyl cellulose, hydroxyethyl cellulose, carboxymethyl cellulose, water soluble polymer such as polyvinyl alcohol, sodium alginate, sodium poly acrylate, polyacrylic ether, polyvinyl pyrrolidone, and a copolymer of isobutylene and maleic anhydride, or biodegradable polymer such as polylactic acid, polybutylene succinate, starch, and dextrin.

The materials may be used either alone or mixed with said materials and formed into a film sheet. Furthermore, repellent such as silicone may be applied or mixed to the film sheet, or laminate processing may be applied to a nonwoven fabric formed with said materials.

A specific example of the water impermeable back face side sheet is a film obtained by preparing polyvinyl alcohol with a specific weight per unit area of 20 to 50 g/m² and to which 0.5 to 5 μm silicone resin or fluorine resin is applied at least on either side and, more preferably, on both sides.

[Mini Sheet Piece]

As the material used for the mini sheet piece, a film made of polyvinyl alcohol, a laminated material of a film made of polyvinyl alcohol and a tissue paper, and the like, can be named.

[Bonding Method]

Also, as a bonding method to be applied to the present invention, a bonding method such as adhesion by polyvinyl alcohol and the like having a water soluble or water swelling performance, heat sealing, or bonding by hydrogen bonding, and the like, can be used either individually or in combination, as appropriate.

INDUSTRIAL APPLICABILITY

According to the present invention as described above, since an interlabial pad is devised to provide an protruded area in a part of a flat area, having an absorbing function, and the ratio of the protruded area and the flat area is controlled accurately, even when the menstrual blood flows along a sloped face of the protruded area, the menstrual blood is absorbed surely by the absorbing function of the flat area, and thereby the danger of leaks due to the menstrual blood flowing outside the pad is reduced. Accordingly, even a high-speed, large-volume menstrual blood, flowing down the body along inner labial walls, can surely be absorbed.

What is claimed is:

1. An interlabial pad for attaching between labia, comprising:
   a water permeable surface side sheet facing a body side;
   either a water permeable or water impermeable back side sheet facing a garment side;
   a water permeable inner sheet positioned between the surface side sheet and the back side sheet; and
   an absorbent body for absorbing body liquid,
   wherein said absorbent body comprises:
      a first absorbent body to form a first protruding area projecting towards the body side from a first flat area, extending along a substantial center line from one end to another end in a longitudinal direction of said interlabial pad;

a second absorbent body to form said first flat area having a substantial plane plate shape, the first protruding area of the first absorbent body has a largest width at a portion closest to said first flat area of the second absorbent body, providing one hollow part on the garment side of said first protruding area formed in a shape corresponding to the first protruding area with a largest width at a portion closest to said first flat area of the absorbent body and extending along the center line from one end to another end with openings at each of the ends, the first absorbent body and the second absorbent body being formed by a single sheet enclosed between the surface side sheet and the inner sheet, and a third base absorbent body which lies on the back side sheet, the second absorbent body being affixed to the third base absorbent body via a portion of the inner sheet;

wherein the surface side sheet, the inner sheet, and the back side sheet are affixed to each other along edges of the interlabial pad in the longitudinal direction, wherein said first flat area and said first protruding area satisfy Formulas (1) to (3) shown below:

$$1 \leq H_1/H_2 \leq 10 \quad (1)$$

$$1/3 \leq W_1/W_2 \leq 5/6 \quad (2)$$

$$1/3 \leq L_1/L_2 \leq 1 \quad (3)$$

where, $H_1$ is the apparent bulkiness of the first protruding area, $H_2$ is the apparent bulkiness of the first flat area, $W_1$ is the apparent maximum width of the first protruding area, $W_2$ is the apparent maximum width of the first flat area, $L_1$ is the apparent maximum length of the first protruding area, and $L_2$ is the apparent maximum length of the first flat area.

2. The interlabial pad as claimed in claim 1, wherein $H_1$ in said Formula (1) is 5 to 30 mm, $W_1$ in said Formula (2) is 2 to 30 mm, $L_1$ in said Formula (3) is 20 to 150 mm.

3. The interlabial pad as claimed in claim 1 or 2, wherein at least fibers for forming said water permeable surface side sheet in said protruding area and that of said first absorbent body are oriented in a lateral direction of said interlabial pad.

4. The interlabial pad as claimed in claim 1 or 2, further comprising an adhesive portion for adhering the interlabial pad to a wearer's genital area on the body side surface of said flat area.

5. The interlabial pad as claimed in claim 1 or 2, wherein the interlabial pad is used together with a sanitary napkin.

6. The interlabial pad as claimed in claim 1 or 2, wherein:
on the garment side of said back side sheet, a mini sheet piece is provided bonding one or more bonding areas in each side in the longitudinal direction of said back side sheet and one or more unbonding areas in the lateral direction of said back side sheet; and
at least one of said one or two unbonding areas, between said mini sheet piece and said back side sheet, forms a finger insertion opening which can directly secure a fingerbreadth opening in the surface direction of said back side sheet.

7. A wrapping body comprising:
an interlabial pad as claimed in claim 6 and
a wrapping container, having a break seal opening, for individually wrapping the interlabial pad,
wherein the interlabial pad is enclosed in the wrapping container;

wherein said interlabial pad is wrapped in said wrapping container so that a finger insertion opening opens towards said opening part; and
wherein said interlabial pad is enclosed in said wrapping container so that said mini sheet piece is folded towards the clothing direction along the substantial center line in the longitudinal direction of said interlabial pad.

8. The interlabial pad as claimed in claim 1 or 2, wherein said interlabial pad is a pad for incontinence of urine.

9. The interlabial pad as claimed in claim 1 or 2, wherein said interlabial pad is an interlabial pad for absorbing vaginal discharge.

10. A wrapping body, comprising:
an interlabial pad as claimed in claim 1 or 2; and
a wrapping container for individually wrapping the interlabial pad wherein the interlabial pad is enclosed in the wrapping container.

11. A wrapping body comprising:
an interlabial pad as claimed in claim 1 or 2 and
a wrapping container, having a break seal opening, for individually wrapping the interlabial pad,
wherein the interlabial pad is enclosed in the wrapping container;
wherein said interlabial pad is wrapped in said wrapping container so that a finger insertion opening opens towards said opening part.

12. The interlabial pad as claimed in claim 1, wherein the absorbent body is enclosed between the water permeable surface side sheet and the either the water permeable or water impermeable back side sheet, which are bonded together.

13. An interlabial pad for attaching between labia, comprising:
a water permeable surface side sheet facing a body side;
either a water permeable or water impermeable back side sheet facing a garment side; and
an absorbent body for absorbing body liquid enclosed between the surface sheet and the back side sheet,
wherein said absorbent body comprises:
a first absorbent body to form a first protruding area projecting towards a body side from a first flat area, extending along a substantial center line from one end to another end in a longitudinal direction of said interlabial pad;
a second absorbent body to form the first flat area having a substantial plane plate shape, the first protruding area of the absorbent body having a largest width at a portion closest to the first flat area of the second absorbent body, the first absorbent body and the second absorbent body being formed by a first unitary absorbent body,
a third base absorbent body to form a second protruding area projecting in a direction opposite to a direction in which the first protruding area protrudes, from a second flat area and extending along a substantial center line in a longitudinal direction of said interlabial pad, and
a fourth absorbent body to form the second flat area having a substantial plane plate shape, the second protruding area of the third base absorbent body having a largest width at a portion closest to the second flat area of the third base absorbent body, the third base absorbent body and the fourth absorbent body being formed by a second unitary absorbent body;
wherein the first unitary absorbent body and the second unit absorbent body are affixed to each other such that the first protruding area and the second protruding area are substantially axisymmetric with regard to the first and second flat areas, wherein the surface sheet and the back side sheet are affixed to each other along edges of the interlabial pad in the longitudinal direction, wherein the first flat area and the first protruding area and the second flat area and the second protruding area satisfy Formulas (1) to (3) shown below:

$$1 \leq H_1/H_2 \leq 10 \tag{1}$$

$$1/3 \leq W_1/W_2 \leq 5/6 \tag{2}$$

$$1/3 \leq L_1/L_2 \leq 1 \tag{3}$$

where $H_1$ is the apparent bulkiness of the first or second protruding area, $H_2$ is the apparent bulkiness of the corresponding first or second flat area, $W_1$ is the apparent maximum width of the first or second protruding area, $W_2$ is the apparent maximum width of the corresponding first or second flat area $L_1$ is the apparent maximum length of the first or second protruding area, and $L_2$ is the apparent maximum length of the corresponding first or second flat area.

14. The interlabial pad as claimed in claim 13, wherein the interlabial pad has a single second protruding area.

15. An interlabial pad for attaching between labia, comprising:

a water permeable surface side sheet facing a body side;

either a water permeable or water impermeable back side sheet facing a garment side; and an absorbent body for absorbing body liquid enclosed between the surface sheet and the back side sheet, wherein said absorbent body comprises:

a first absorbent body to form a first protruding area projecting towards a body side from a first flat area, extending along a substantial center line from one end to another end in a longitudinal direction of said interlabial pad;

a second absorbent body to form said first flat area having a substantial plane plate shape, the first protruding area of the absorbent body having a largest width at a portion closest to the first flat area of the second absorbent body, the first absorbent body and the second absorbent body being formed by a first unitary absorbent body, a third base absorbent body to form a second protruding area projecting in a direction opposite to a direction in which the first protruding area protrudes, from a second flat area and extending along a substantial center line in a longitudinal direction of said interlabial pad, and a fourth absorbent body to form the second flat area having a substantial plane plate shape, the second protruding area of the third base absorbent body having a largest width at a portion closest to the second flat area of the third base absorbent body, providing a hollow part in a direction opposite to a direction in which the first protruding part protrudes, formed in a shape corresponding to the second protruding area with a largest width at a portion closest to the first flat area of the fourth absorbent body extending along the center line from on end to another end with openings at each of the ends, the third base absorbent body and the fourth absorbent body being formed by a second unitary absorbent body;

wherein the first unitary absorbent body and the second unitary absorbent body are affixed to each other such that the first protruding area and the second protruding area are substantially axisymmetric with regard to the first and second flat areas, wherein the surface sheet and the back side sheet are affixed to each other along edges of the interlabial pad in the longitudinal direction, wherein the first flat area and the first protruding area and the second flat area and the second protruding area satisfy Formulas (1) to (3) shown below:

$$1 \leq H_1/H_2 \leq 10 \tag{1}$$

$$1/3 \leq W_1/W_9 \leq 5/6 \tag{2}$$

$$1/3 \leq L_1/L_2 \leq 1 \tag{3}$$

where $H_2$ is the apparent bulkiness of the first or second protruding area, $H_2$ is the apparent bulkiness of the corresponding first or second flat area, $W_1$ is the apparent maximum width of the first or second protruding area, $W_2$ is the apparent maximum width of the corresponding first or second flat area, $L_1$ is the apparent maximum length of the first or second protruding area, and $L_2$ is the apparent maximum length of the corresponding first or second flat area.

* * * * *